United States Patent
Virshek et al.

(10) Patent No.: US 10,039,589 B2
(45) Date of Patent: Aug. 7, 2018

(54) ENFORCEMENT DEVICE FOR LIMITED USAGE PRODUCT

(71) Applicant: Gyrus ACMI, Inc., Southborough, MA (US)

(72) Inventors: Michael A. Virshek, Rogers, MN (US); Riyad Moe, Waunakee, WI (US); Richard J. Curtis, Maple Grove, MN (US); David C. Church, Millington, TN (US)

(73) Assignee: Gyrus ACMI, Inc., Southborough, MA (US)

(*) Notice: Subject to any disclaimer, the term of this patent is extended or adjusted under 35 U.S.C. 154(b) by 29 days.

(21) Appl. No.: 14/682,255

(22) Filed: Apr. 9, 2015

(65) Prior Publication Data

US 2015/0289924 A1 Oct. 15, 2015

Related U.S. Application Data

(60) Provisional application No. 61/977,319, filed on Apr. 9, 2014.

(51) Int. Cl.
*A61B 18/18* (2006.01)
*A61B 18/12* (2006.01)
*A61B 18/00* (2006.01)

(52) U.S. Cl.
CPC .............. *A61B 18/1233* (2013.01); *A61B 2018/00773* (2013.01)

(58) Field of Classification Search
CPC ........ A61B 18/1445; A61B 2018/1455; A61B 2019/4873; A61B 18/1233;

(Continued)

(56) References Cited

U.S. PATENT DOCUMENTS 5,313,935 A * 5/1994 Kortenbach ....... A61B 1/00105
 116/221
5,400,267 A * 3/1995 Denen ................. A61B 17/00
 128/908

(Continued)

OTHER PUBLICATIONS

International Search Report, PCT/US2015/025048, pp. 3.

*Primary Examiner* — Michael Peffley
*Assistant Examiner* — Amanda Zink
(74) *Attorney, Agent, or Firm* — Chapin IP Law, LLC

(57) ABSTRACT

A surgical device employs a longevity circuit for preventing operation after a specified time based on safe use expectations. The surgical device delivers a therapy signal via a handpiece having electrodes in proximity to the surgical site. The therapy signal is a high frequency electrical signal delivered from a generator coupled to the handpiece, and activated by a control signal. A therapy circuit established by coupling the handpiece and generator delivers the therapy signal, and is monitored for activation based on a time since a first activation, a number of activations, or an aggregate time of activated intervals. A usage limit defines the activation lifespan, and is employed for monitoring either the therapy circuit or the control circuit, to determine a usage history. Following expiration of a safe usage limit, a longevity circuit in the handpiece disables the handpiece for successive uses, and is independent of a connection to a particular generator.

12 Claims, 8 Drawing Sheets

(58) Field of Classification Search
CPC ....... A61B 2018/00773; A61L 2202/24; A61L 2/00; A61L 2/02; A61L 2/04; A61L 2/07; A61L 2/16; A61L 2/18; A61L 2/202; A61L 2/204; A61L 2/206
See application file for complete search history.

(56) References Cited

U.S. PATENT DOCUMENTS

| | | | |
|---|---|---|---|
| 5,991,355 A * | 11/1999 | Dahlke | A61B 18/14 377/15 |
| 6,295,330 B1 * | 9/2001 | Skog | A61L 2/28 377/15 |
| 6,387,092 B1 * | 5/2002 | Burnside | A61B 18/0218 606/20 |
| 8,460,284 B2 | 6/2013 | Aronow et al. | |
| 2003/0208196 A1 * | 11/2003 | Stone | A61B 18/14 606/41 |
| 2004/0092992 A1 | 5/2004 | Adams et al. | |
| 2007/0215001 A1 * | 9/2007 | Voegele | C09D 11/50 106/31.01 |
| 2009/0054889 A1 | 2/2009 | Newton et al. | |
| 2009/0065565 A1 * | 3/2009 | Cao | A61B 18/1402 235/375 |
| 2010/0280511 A1 * | 11/2010 | Rachlin | A61B 18/1445 606/34 |
| 2011/0238063 A1 | 9/2011 | Gregg | |
| 2013/0046299 A1 | 2/2013 | Newkirk | |
| 2013/0289559 A1 * | 10/2013 | Reid, Jr. | A61B 18/1477 606/41 |
| 2014/0060161 A1 * | 3/2014 | Schick | G01N 37/00 73/53.01 |

\* cited by examiner

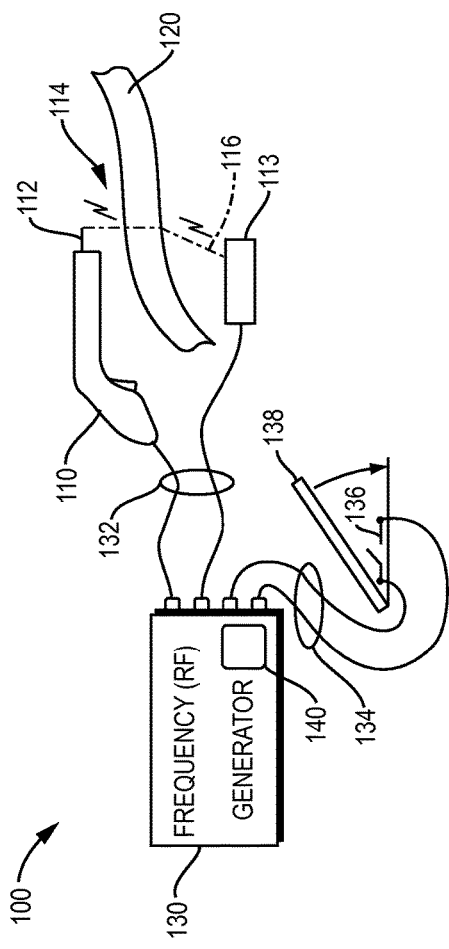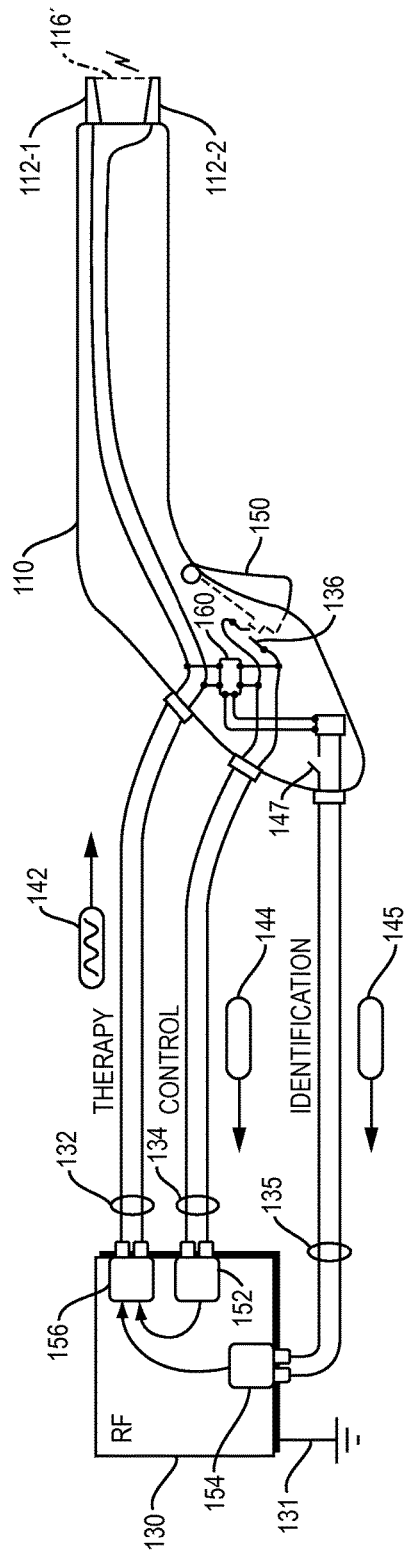

ENFORCEMENT DEVICE FOR LIMITED USAGE PRODUCT

RELATED APPLICATIONS

This patent application claims the benefit under 35 U.S.C. § 119(e) of U.S. Provisional Patent App. No. 61/977,319, filed Apr. 9, 2014, entitled "SURGICAL DEVICE PRODUCT LIFESPAN," incorporated by reference in entirety.

BACKGROUND

Electrical surgical devices employ electrodes for delivering a high-frequency electric source to a surgical site for manipulating tissue by cutting or obliterating the surgical material. Such electrosurgical devices include a frequency, or RF generator for providing the high frequency (AC) electrical signal, and a handpiece including one or more electrodes for delivering a therapy signal in the form of electric current (voltage). At least one electrode carries the therapy signal delivered proximate to the tissue area, and a second electrode or ground pad at a different potential completes the therapy circuit for providing a current path through the surgical material (tissue). The signal is of a high enough frequency that it avoids interference with the native CNS (central nervous system) of the patient, and may take the form of a monopolar (i.e. single electrode with grounding pad) or bipolar electrodes which co-locate two or more electrodes on the same handpiece, thus localizing the electrical energy. The monopolar/bipolar approach, as well as frequency and voltage level, vary based on therapeutic factors, such as whether excision, cutting, obliteration, or cauterization is desired. Often, the handpiece and RF generator are separate components and may be interchanged depending on coordination of physical electrical couplings, such as plugs.

SUMMARY

A surgical device may employ a lifetime or longevity circuit for preventing operation after a specified time based on safe use expectations. The surgical device delivers a therapy signal via a handpiece having electrodes in proximity to the surgical site. The therapy signal is a high frequency electrical signal delivered from a generator coupled to the handpiece, and activated by a control signal. A therapy circuit established by coupling the handpiece and generator delivers the therapy signal, and is monitored for activation based on a time since a first activation, a number of activations, or an aggregate time of activated intervals. Activation energizes the electrode and is usually in response to a user control, such as a foot pad or finger trigger. A usage limit defines the activation lifespan, and is employed for monitoring either the therapy circuit or the control circuit, to determine a usage history. Following expiration of an intended usage limit, a longevity circuit in the handpiece disables either the control circuit or the therapy circuit so that the electrode cannot be energized for successive uses. The usage limit applies independently of connection to a particular generator, and the longevity circuit identifies the usage threshold for disablement regardless of the generator connection.

Electrosurgical devices apply a specialized electric current to a surgical site for tissue manipulation such as excision, cutting, and cauterization. A variety of treatment options are encompassed by various arrangements of electrodes, voltage, and frequency, however, generally the electrode provides a therapy signal in the form of a high frequency voltage. A second electrode, at a different voltage, is either adjacent (in a bipolar arrangement) or in proximate contact with the surgical site (in a monopolar arrangement). A therapy circuit connects to the electrode for providing the therapy signal from an RF generator (generator), which provides a precise oscillation at the prescribed voltage depending on the treatment parameters. The therapy circuit is switched on from a control circuit or activation circuit, typically via a foot pedal or finger trigger on the device, however any suitable activation mechanism may be employed.

The generator connects to the handpiece through one or more connections, which may or may not be a standardized/molded connector, hence the generator and handpiece are not necessarily a matched pair. An optional identification (ID) circuit may provide feedback from the handpiece indicative of device compatibility.

While many surgical instruments are designated as single use, or otherwise undergo a rigid sterilization schedule to ensure each patient receives fresh equipment, conventional electrosurgical instruments provide no enforcement as to the duration of use or reuse of the handpiece and corresponding electrode. While the generator is a non-sterile hardware item intended for multiple uses, the handpieces are directly in the surgical field and require greater scrutiny for safe operation. Configurations herein are based, in part, on the observation that conventional electrosurgical instruments may be reused beyond a safe lifetime, compromising patient safety.

Further, since there might not be matching between handpieces and RF generators, enforcement features which rely on the consistent use of a particular generator might be inoperable if the handpiece is used with a different generator. Hence enforcement or longevity logic should be operable within the handpiece alone. Unfortunately, conventional approaches to electrosurgical device usage suffer from the shortcoming that reuse beyond an intended product lifespan or usage cycle cannot be performed effectively by the generator, since handpieces are generally interoperable among multiple generators, given sufficient electrical connections.

Accordingly, configurations herein substantially overcome the above described shortcomings of handpiece reuse by disposing a longevity circuit in the handpiece for identifying usage and disabling or terminating the handpiece when the safe usage cycle has been exhausted.

In further detail, in a surgical device having an electrode for manipulating surgical material, configurations herein perform a method for controlling a surgical device by activating a therapy circuit in response to a control circuit, in which the therapy circuit is for energizing an electrode, and determining, based on an deactivation pattern, that a usage limit has been met. The deactivation pattern is indicative of at least one of exceeding a time limit since a first activation, exceeding a number of activations, or exceeding an aggregate time of activation. Upon determining that the usage limit has been reached, the method de-energizes the electrode.

In a particular configuration, suited to a monopolar medical device, included is an electrode responsive to a generation source, such that the electrode configured to selectively deliver a therapeutic current, and a termination circuit, the termination circuit interrupting the delivered therapeutic current after a deactivation pattern, the deactivation pattern based on monitoring the electrode. The deactivation pattern is determined independently of a source of the therapeutic current, such that the termination is not dependent on connection to any particular frequency generator.

The approach may be extended to a bipolar configuration, such that the electrode is a therapy electrode responsive to the therapy circuit, and further including a second electrode, typically parallel and in close proximity, such that the ground electrode for completing the therapy circuit for providing the therapeutic current to a patient (in contrast to an external ground pad as may be employed with a monopolar device).

Typical configurations include the control circuit, also known as an activation circuit, such that the activation circuit is responsive to an operator input for energizing the therapy circuit. Monitoring and/or termination may be performed on either the therapy circuit or the activation circuit. Also, circuit termination may also be performed on an ID circuit. In such an approach, the medical device includes an electrode responsive to a generation source, in which the electrode is configured to selectively deliver a therapeutic current, and a termination circuit, such that the termination circuit interrupts the delivered therapeutic current after a deactivation pattern. The activation circuit is responsive to an operator input for energizing the therapy circuit, and the termination circuit may be configured to interrupt the therapeutic current by disabling the activation circuit.

BRIEF DESCRIPTION OF THE DRAWINGS

The foregoing and other objects, features and advantages of the invention will be apparent from the following description of particular embodiments of the invention, as illustrated in the accompanying drawings in which like reference characters refer to the same parts throughout the different views. The drawings are not necessarily to scale, emphasis instead being placed upon illustrating the principles of the invention.

FIG. 1 shows a context view of an electrosurgical system suitable for use with the disclosed configurations;

FIG. 3 shows a functional block diagram of a surgical device operable according to the method of FIG. 2;

DETAILED DESCRIPTION

Figure 2:
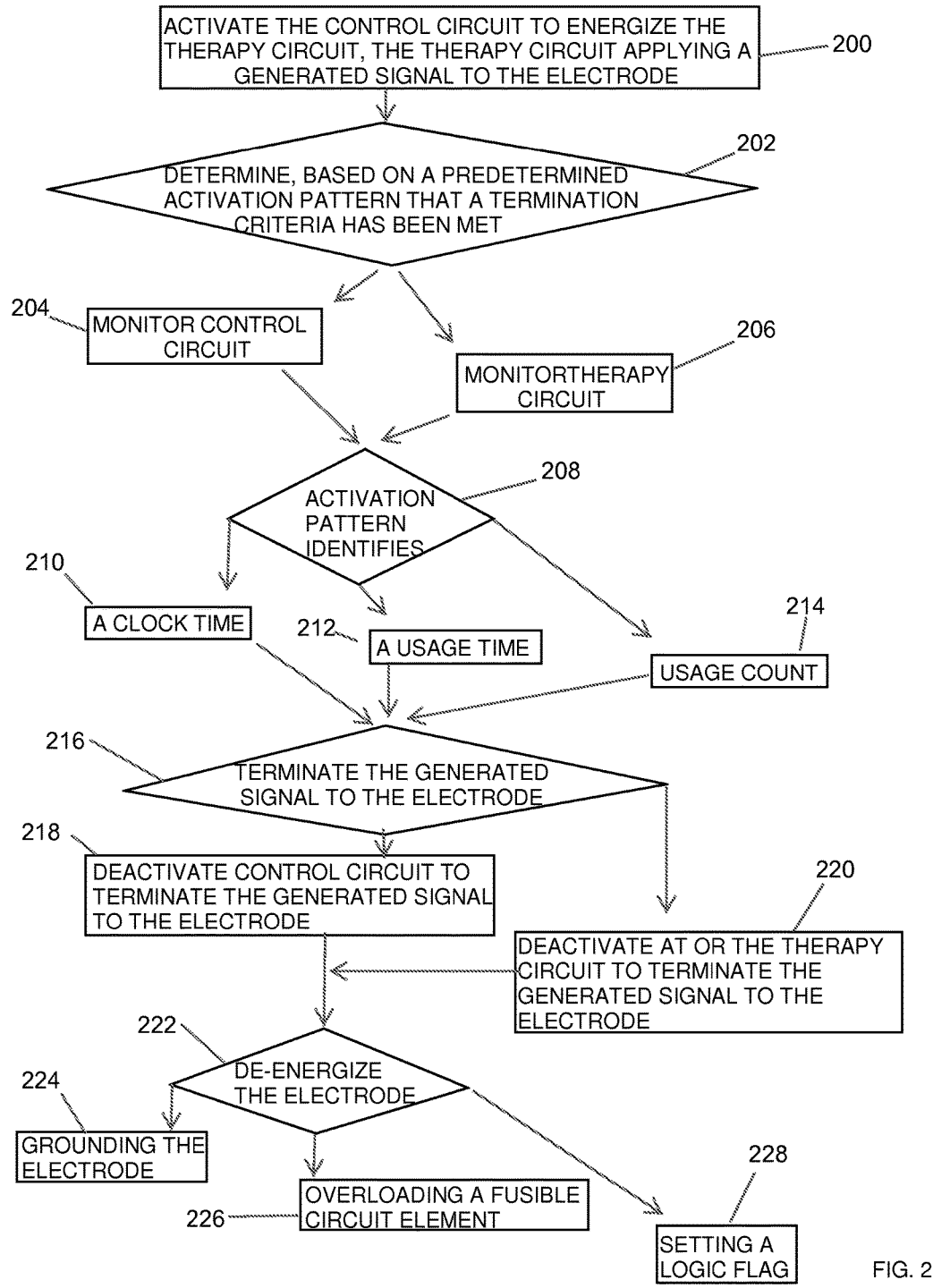
FIG. 2 is a flowchart of surgical device operation of the system of FIG. 1.

The figures below depict various example configurations of the electrosurgical device as depicted herein. The examples show a particular configuration, and other configurations may achieve the results shown through other physical arrangements. The electrosurgical device is most often employed in a hospital environment, however any suitable medical facility will suffice. In the illustrated examples, monopolar and bipolar examples are depicted, and activation controls include a foot pedal and finger trigger, however alternate approaches may be employed for circuit activation.

In contrast to conventional approaches, the example configurations herein provide a circuit that commences countdown at first use, rather than power on or removal of a pull tab. First use is detected based on identification of actual usage of the surgical device on a patient, rather than by an indirect act. Configurations herein provide a therapy circuit that reads a signal in a switching circuit and then disables a power circuit, or vice versa. The disclosed configurations also provide a countdown circuit that disables a device by altering the AC response characteristics of the switching circuit so that the generator interprets an error state.

For example, in US Pub. No. 2011/0270179 (Ouyang, et al), a timer 184 is pre-programmed to run a predetermined length of time before programming the DB bit of the OTP chip 114. In Ouyang '179, when a countdown timer expires it programs a chip that blocks a digital image signal. It does not interrupt a power signal or an activation switch signal. In contrast to the proposed approach, the timing window is an absolute elapsed time from a power-on event, not tied to a surgical use. Further, the disclosure pertains to an endoscope system, and it is not clear how the chip is aware of the power on event. In contrast, in the disclosed approach, the trigger can be the first activation signal or first therapy energy delivery.

US Publication 2010/0280511 (Rachlin et al) teaches an electrosurgical instrument includes a housing having a treatment portion attached thereto. The treatment portion is adapted to connect to an electrosurgical generator that supplies energy to the electrosurgical instrument. However, a timing circuit may be initiateable upon removal of a timing pin, an electrically insulative cover and/or a battery sleeve. Rachlin '511 therefore differs because it is not triggered by initial electrical signal, and the means of timer initiation are not closely tied to a detected first surgical use, and uses a static, absolute timing window of usage.

U.S. Pat. No. 7,879,032, to Garito et al., suggests a timer in the form of an activating battery with a known discharge rate such that the battery voltage gradually reduces in value with use. In contrast to the disclosed approach, Garito '032 employs a triggering event defined by pulling out a non-conductive tab from the battery contact. Further, Garito requires the additional power requirement of a battery.

U.S. Pat. No. 8,046,082, to Herregraven et al., suggests a nerve stimulator such that once a particular set of criteria is met that determines that the lead set should not be reused, the fuse is deliberately blown, and the two particular connections no longer conduct electricity from one to the other. Herregraven, however, requires a proprietary generator with a state sensing circuit and an ability to overpower the state circuit. In contrast, the approach disclosed herein is entirely self-contained within the handpiece device.

In U.S. Pub. No. 2012/0191091 (Allen), an electrosurgical instrument includes a housing assembly having a first disposable treatment portion selectively attached thereto. The disposable treatment portion is adapted to connect to an electrosurgical generator that supplies energy to the electrosurgical instrument. Allen '091 also includes a control circuit including a sensor(s) that detects mechanical actuation of the trigger assembly, mechanical actuation of a jaw closure assembly, the removal of the first disposable treatment portion and/or the insertion of an unused subsequent disposable treatment portion. Allen, therefore, is limited to detection of mechanical events for assessing usage, not electrical signals, and employs no timer, rather usage is tracked by the count of discrete mechanical events device.

U.S. Pat. No. 4,624,578, to Green, teaches a system in which rental equipment such as television sets are provided with a timer which operates a relay to connect power to the equipment only during the time for which rental has been paid. The Green '578 system employs a single window time parameter, and further, programmed countdown is not part of the manufacturing process of the device, but rather based on an external transaction (rental contract).

FIG. 1 shows a context view of an electrosurgical system suitable for use with the disclosed configurations. Referring to FIG. 1, in a surgical environment 100, a surgical instrument takes the form of a handpiece 110 having one or more electrodes 112 for activation adjacent to a surgical site 114. The electrode 112 discharges a therapy signal 116 for manipulating surgical tissue 120 (tissue), to cut, cauterize, ablate, or otherwise dispose the tissue 120. Typically, the surgical material is tissue and the electrode 112 is in communication with a ground such that the surgical material is disposed between the electrode and the ground, for cutting, debriding or otherwise manipulating tissue in any suitable manner to the procedure being performed. In the example of FIG. 1, a ground plate 113, disposed in a proximate area of the tissue 120, completes the therapy circuit, representing a ground or lower potential than the energized electrode 112.

The electrode 112 connects to a generator 130 for receiving the high frequency therapy signal 116 via a therapy circuit 132. A control circuit, or activation circuit, 134 includes a switch 136, such as a foot pedal 138, for turning on the generator 130 via a relay 140 or other activation mechanism for activating the therapy circuit 132 and energizing the electrode 112. The generated signal 116 is an AC signal adapted for manipulating tissue without inducing muscular activity by mimicking neurosignals. While the term "RF" is commonly used to denote the high frequency, it should be apparent that the generator produces an AC electrical signal rather than a radio transmission signal.

FIG. 2 is a flowchart of surgical device operation of the system of FIG. 1. Referring to FIGS. 1 and 2, in a surgical device such as the handpiece 110 having a therapy circuit 132 and a control circuit 134, in which the therapy circuit 132 is responsive to the control circuit 134 for energizing an electrode 112 to manipulate surgical material or tissue 120, the method for controlling the surgical device as disclosed herein includes, at step 200, activating the control circuit 134 to energize the therapy circuit 136, such that the therapy circuit 136 applies a generated signal 116 to the electrode 112. The handpiece 110 determines, based on a predetermined deactivation pattern of either the control circuit 134 or the therapy circuit 132, that a termination criteria indicating a usage limit or product lifespan has been met, as shown at step 202. As indicated above, the control circuit 134, or activation circuit operates to energize the therapy circuit for manipulating tissue. The energized circuit may also control any suitable powered element or device.

The handpiece may monitor either the control or therapy circuits for determining the deactivation pattern, as shown at steps 204 and 206, respectively. The determined deactivation pattern (step 208) may identify either a clock time, as depicted at step 210, a usage time, as depicted at step 212, or a usage count, as depicted at step 214. The deactivation pattern generally starts from a time of first use, such as when the control circuit is first actuated. A clock time represents an absolute passage of time from the first activation, regardless of how often or how much the handpiece 110 is used. This approach may permit successive uses if procedures are closely spaced in time. A usage time counts only the time that the handpiece 110 is energized, that is, actively cutting/manipulating tissue. Since different surgical procedures, as well as different patients, may require varying degrees of cutting or obliteration, the usage time benefits from matching to the procedure. The usage count 214 approach counts the number of times the trigger 150 or foot pedal 138 is pressed to energize the electrode 112 for a cutting operation, independently of the length of time it remains energized. Since a single cut may be short or may maintain the electrode in an energized state for some time, it is beneficial to match the number of activations required in a particular procedure, so that the handpiece does not reach the usage limit during a procedure.

Once the termination criteria has been met, the handpiece 110 terminates the generated signal 116 to the electrode 112, as shown at step 216. Termination of the generated signal may be done by either deactivating the control circuit 134, as depicted at step 218, or the therapy circuit 132, as depicted at step 220, to terminate the generated signal to the electrode. De-energizing the electrode at step 222 may then be performed by either grounding the electrode, as shown at step 224, overloading a fusible circuit element, as depicted at step 226, or setting a logic flag for a circuit or instruction sequence to operate on, as shown at step 228.

Therefore, the control circuit 134 and responsive therapy circuit 132 interoperate to enforce the usage limit. Depending on the configuration, enforcement may include determining the deactivation pattern of the control circuit 134 and terminating the generated signal 116 by disabling the control circuit 134, or determining the deactivation pattern of the therapy circuit 132 and terminating the generated signal 116 by disabling the control circuit 134. An alternate enforcement operates on the therapy circuit, thus determining the deactivation pattern of the control circuit 134 and terminating the generated signal 116 by disabling the therapy circuit 132, or determining the deactivation pattern of the therapy circuit 132 and terminating the generated signal 116 by disabling the therapy circuit 132.

FIG. 3 shows a functional block diagram of a surgical device operable according to the method of FIG. 2. In an example arrangement, a high frequency (HF) electrosurgical excision tool is embodied, however any suitable electrical surgical instrument may be employed, such as surgical excision tools, debrider, drills, saws, pumps and other rotary and/or motor driven instruments or tools. Referring to FIGS. 1 and 3, the handpiece 110 may also take the form of a bipolar instrument having a plurality of electrodes 112-1 . . . 112-2 (112 generally), such that the therapy signal 116' travels to the electrode 112-2 of lower potential (often referred to as a return electrode), rather than the ground plate 113. FIG. 3 shows the therapy circuit 132 and control circuit 134 connections from the generator 130 to the handpiece 110. The therapy circuit 132 carries an AC signal 142 at a sufficiently high voltage to affect the tissue 120. The control circuit 134 carries an enablement signal 144 upon activation by the switch 136', which may be closed by a finger trigger 150. An optional identification circuit 135 carries identification information 145, which may be matched at the generator 130 before activating the therapy circuit 132. The ID circuit 135 may simply be a switch 147 closure when the handpiece 110 is connected to the generator 130, or may represent a more complex exchange of handpiece model type and operating parameters. In usage, the generator 130 invokes the identity circuit 135 for performing a comparison between the handpiece and the generator 130 for powering the therapy circuit 132. Based on the comparison, the handpiece 110 enables the generated signal if a match is found between the handpiece and the RF generator, and the ID circuit 135 results in blocking the generated signal if a match is not found. The identification circuit 135 therefore receives an expected response from the RF generator 130, or terminates the therapy circuit 132 upon lack of receipt of the expected response.

A control circuit status (typically open or closed) 152 and ID circuit status 154 send an enablement signal to control the therapy circuit status 156. In other words, the therapy circuit 132 is responsive to the control 134 and ID 135 circuits to energize the electrodes 112. The electrodes may employ a direct ground 131 connection or may employ a second electrode 112-2 for varying the potential in accordance with a desired AC signal.

The handpiece 110 includes an enablement module 160 which monitors the control, ID and therapy circuits 132, 134, 135 to maintain usage history and identify when the usage limit is reached, discussed further below in FIG. 4.

Figure 4:
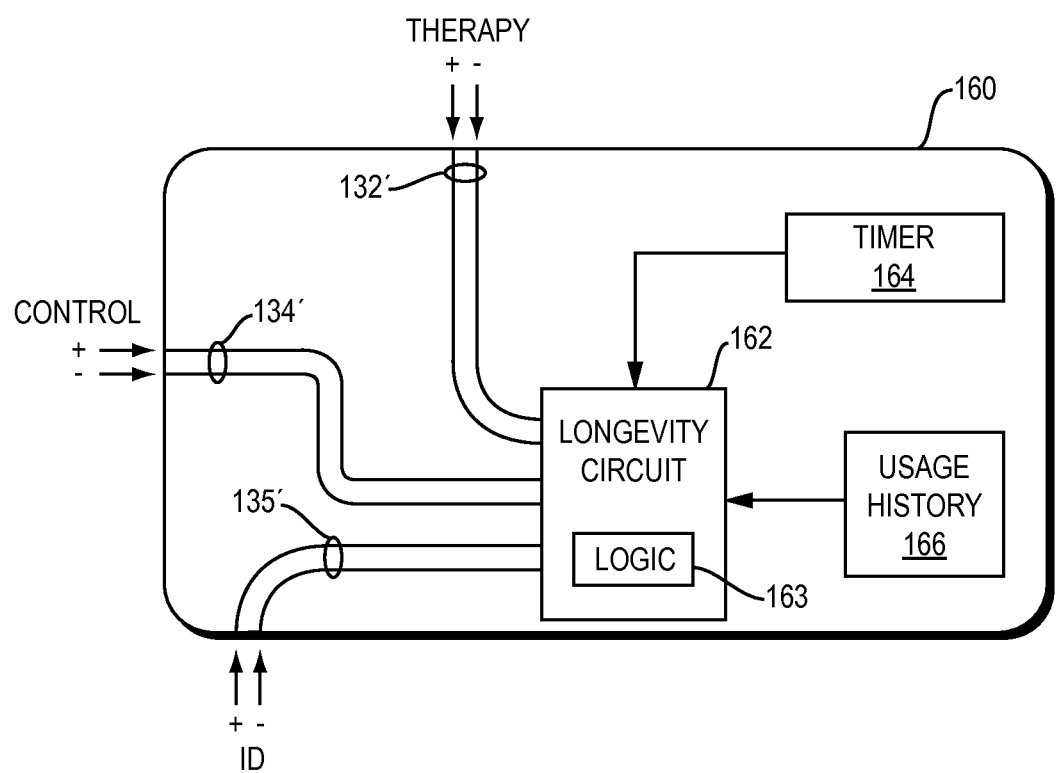
FIG. 4 shows the longevity circuit of FIG. 3 in greater detail.

FIG. 4 shows the longevity circuit of FIG. 3 in greater detail. Referring to FIGS. 1, 3 and 4, the enablement module 160 is included entirely in the handpiece 110 so as not to be dependent on any particular generator 130 for computing and affecting the usage limit. The enablement module 160 includes a longevity circuit 162, which receives information from a timer 164 and a usage history 166 gathered from previous activations (activation history). The longevity circuit 162 connects to each of the therapy 132, control 134 and ID circuits 135, as shown by respective leads 132', 134' and 135,' for monitoring and manipulating the respective circuits. For example, one approach to disabling the electrodes 112 is to ground the positive (supply) side. Alternatively, de-energizing the electrode may include of grounding the electrode 112, overloading a fusible circuit element or setting a logic flag. The longevity circuit 162 includes logic 163 for determining an activation history of the handpiece 110 based on activation of the handpiece 110 from an energizing signal (therapy circuit), and disabling the electrode handpiece 110 based on the activation history attaining a predetermined usage limit. The logic 163 compares, at each activation of the handpiece 110, the activation history 166 of the handpiece 110 to the predetermined usage limit, and disables the handpiece 110 when the usage history exceeds the usage limit. Comparison of the activation history to the predetermined usage limit includes determining if the handpiece/electrode usage is exceeding a time limit since a first activation, exceeding a number of activations, or exceeding an aggregate time of activation.

The enablement module 160 may take a variety of forms, such as a hardwired circuit, an IC (integrated circuit) module with processor control and stateful operations and instructions, or a combination. Whether by IC or hardwired elements, the handpiece 110 identifies an initial activation, such as a first power-up, and determining the deactivation pattern based on the initial activation.

The enablement module 160 is contained entirely within the handpiece 110, thus removing variability of corresponding generators 130 from affecting enforcement of the longevity circuit. The enablement module 160 may take any suitable physical form for monitoring and enforcing the usage limit. The example arrangement of FIGS. 1, 2 and 4 includes surgical apparatus comprising an RF generator 130 for generating an oscillating signal at a predetermined frequency, a control circuit 134 for activating the RF generator 130 in response to usage signals 144, such as from the finger trigger 150 or foot pedal 138, and a therapy circuit 132, responsive to the control circuit 134 for activation, in which the therapy circuit 132 receives the generated oscillating signal (therapy signal 116). The electrode 112 is attached to the handpiece 110, such that the handpiece 110 is responsive to an operator for disposing the electrode at the surgical site 114, typically by moving the electrode 112 adjacent to the surgical site 114. The electrode 112 connects to the therapy circuit 132 for delivering the oscillating signal to the surgical site 114, and the longevity circuit 162 provides a selective switching mechanism, such that the switching mechanism is operable to terminate operation of the therapy circuit.132, directly or by intervening in the control circuit 134, according to the approaches outlined herein. In particular arrangements, the handpiece 110 includes at least a portion of the control circuit 134, and an activation switch on the handpiece 110, such as finger trigger 150, is responsive to an operator input for activating the control circuit 134.

The longevity circuit 162 enforces the usage limit by deactivating at least one of the therapy circuit 132 or the control circuit 134. Depending on the configuration, disabling the handpiece 110 may include modifying the handpiece 110 to ignore the energizing signal without communicating with the frequency generator 130. Therefore, the handpiece is operable with various generators 130 without compromising the longevity circuit 162. Further, disabling the handpiece retains full functionality in the frequency generator 130.

It should be emphasized that the various configurations of the longevity/termination circuit may be implemented in various forms of the therapy circuit, such as monopolar, bipolar, and ground pad arrangements, and are further interoperable with the detection circuit and optionally, with the identity circuit in any suitable combination. For example, the termination circuit employing elapsed time, intervals of time, or counts of activation may be employed with monopolar, bipolar, and with or without an identity circuit, and activated by a foot pedal, hand trigger, or other suitable activation. Such alternate configurations are listed below in an example but non-exclusive rendering; alternate configurations of the termination circuit and application to various devices may be envisioned by those of skill in the art.

The termination circuit may operate by identifying a deactivation pattern when a detected usage indicates initiation or completion of a first usage in a surgical procedure, using events that necessarily accompany such an occurrence such as energizing the surgical tool. Usage may therefore be based on a first sensing of a therapeutic current through the electrode, and an aggregate duration of therapeutic current delivery through the electrode. An aggregate usage identifies a series of short periods of activation (energizing the electrode), such as when a surgeon is making a series of incisions separated by removal of excised material. Usage may also be based on a first sensing of a therapeutic current through the electrode, and an elapsed time following the first sensing. Such an approach presumes a particular time period for the surgical procedure, regardless of the number of durations of usage periods within the surgical procedure. Alternatively, detected usage may be based on a number of activations of the electrode, such that the activations defined by a delivery of a therapeutic current through the electrode followed by an absence of the therapeutic current. Each activation may then be of a varied duration, resulting in a variable total usage time, since each activation (i.e. hand trigger or foot pedal press) is the observed metric. The termination circuit may also be configured to modify characteristics of the therapy circuit for providing a source of the therapy circuit with a response corresponding to termination of the therapy circuit, such as closing a switch that increases the current flow such that the termination circuit observes a short circuit indication or other excessive current flow.

Figure 5:
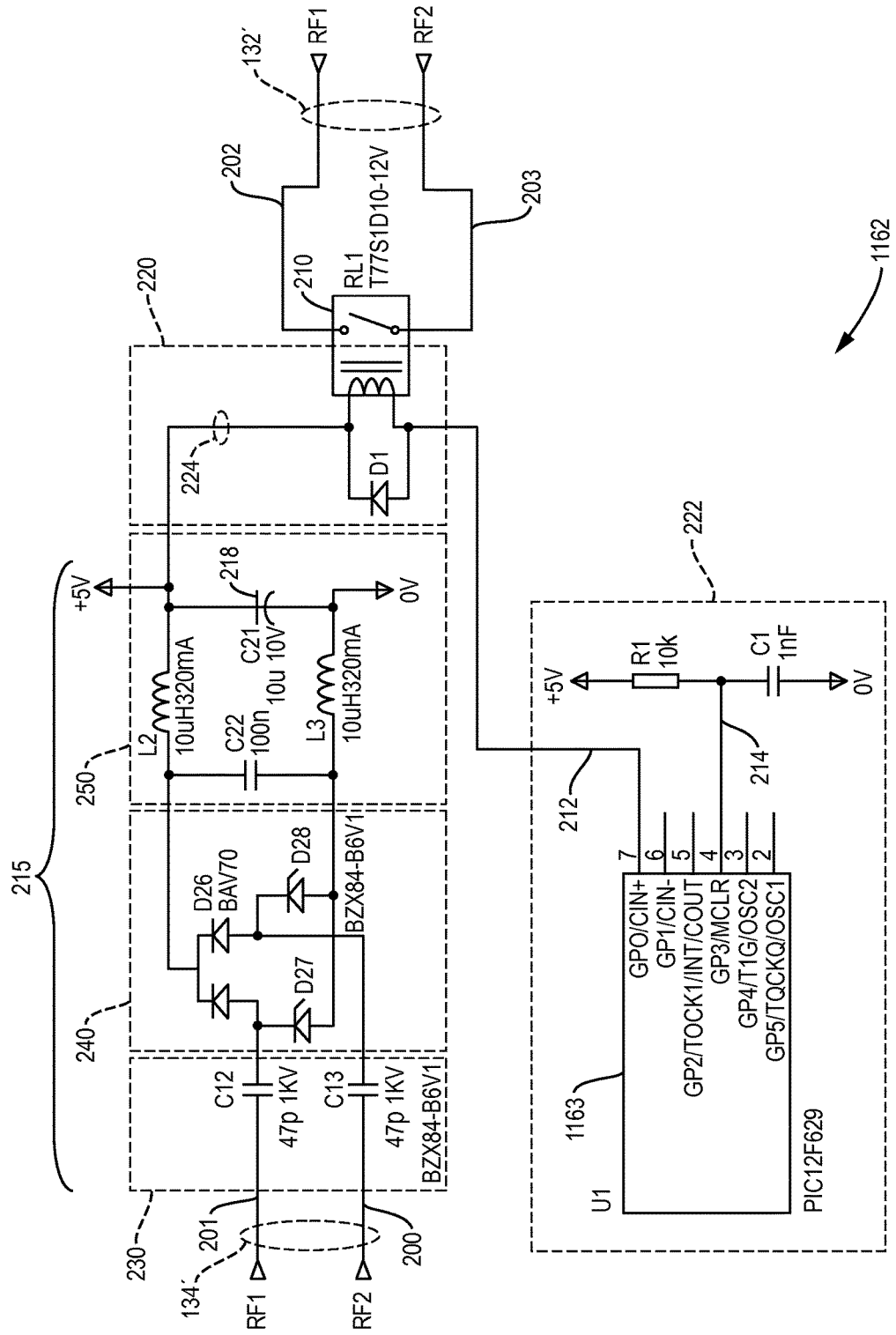
FIG. 5 shows a longevity circuit in greater detail including a termination circuit and an activation circuit.

FIG. 5 shows a particular configuration of a longevity circuit 162 defined by a termination circuit 1162 including a monitoring circuit 215 and a deactivation circuit 222. Referring to FIGS. 4 and 5, the longevity circuit 162 initiates and terminates operability of the therapy circuit 132' to correspond to the desired usage pattern, such as a single use/procedure device 110. It should be noted that localized operation of the termination circuit 222 within the device 110 is beneficial, to avoid bypassing the termination circuit by driving the device 110 from a different generator. Accordingly, the therapy circuit 132' and also the control circuit 134' and the ID circuit 135', if present all pass through the longevity circuit 162 in the handheld device 110. The longevity circuit 162 includes the deactivation circuit 222. In other words, the termination circuit may be captured in the medical device and not disposed in the console with the power source and the power source controller, so that the handheld medical device remains autonomous against defeat by reconnection to an alternate console/power supply, for example. In the example configuration of FIG. 5, a switching circuit 220 is responsive to the deactivation circuit 222 for effectively preventing current flow in the therapy circuit by disabling the relay 210.

The termination circuit 1162 includes a programmable integrated circuit, typically in the form of a chip 1163 representing control logic 163, a relay 210, and a storage capacitor 218.

The termination circuit 1162 further includes a pair of coupling capacitors 230. The coupling capacitors 230 may be used to reduce the voltage drop across the leads 200, 201. Leads 200 and 201 may be the two leads of the therapy circuit 132'. Alternatively leads 200 and 201 may be the two leads of an activation circuit 134'. The termination circuit 1162 may also include a diode bridge circuit 240. The diode bridge circuit 240 rectifies the AC signal to produce a DC signal. The termination circuit 1162 may also contain (smoothing) capacitors and inductors 250 to refine the signal, including the storage capacitor 218. In one example, the coupling capacitors 230, diode bridge circuit 240 and cleaning capacitor and inductors 250 may produce a clean DC signal 224 of a set voltage, such as 5.1 V, and define the monitoring circuit 215. The DC signal 224 operates with the deactivation circuit 222 to deactivate and disable the therapy circuit 132', as now discussed below.

With respect to the system, methods and operations depicted in FIGS. 3-5, the longevity circuit 162 monitors the device 110 usage via either the therapy circuit 132' activation or the control circuit 134' activation, and disables the therapy circuit in based on usage meeting a deactivation pattern. The termination circuit 1162 of FIG. 5 is a particular configuration of a longevity circuit 162 (FIG. 4). The monitoring circuit 215 defines the portion of the longevity circuit 162 that identifies the predetermined deactivation pattern indicative of device usage that exceeds a proscribed manner of usage, typically exceeding a single procedure use. The deactivation circuit 222 performs the switching that results in a non-activated device by removing the ability of the therapy circuit 132' to apply therapeutic voltage. These circuits and related operations will become more apparent with respect to the discussion of FIGS. 6a-10 below, pertaining to specific configurations.

In the example configuration of FIG. 5, the termination circuit 1162 defines the logic 163 via a programmable integrated circuit chip 1163. The programmable chip 1163 may have two input leads for power 214 and an output 212. The programmable chip 1163 may be programmed to count to a predetermined value. Prior to reaching the count value the programmable integrated circuit 1163 may produce an output with a predetermined value, for example +5V. Upon reaching the count value, the chip 1163 may produce an output with a different predetermined value, for example 0V to cause the relay 210 to disable the therapy circuit 132'.

In the example of FIG. 5, the circuit 162 includes relay 210. The relay 210 may be connected on one side to the high side of the DC voltage signal 224 and to the other side to the output 212 from the chip. The relay 210 may be a normally open relay. Prior to the chip 1163 reaching a present value there may be a zero, or near zero, voltage drop across the relay and thereby keeping it in an open state. Upon reaching the count value defined by the predetermined deactivation pattern, the voltage across the relay may increase above the tripping threshold of the relay and the relay 210 would close. In one embodiment as shown, the relay 210 closes to cause a shorting condition across the leads 202, 203 of the therapy circuit 132'. In this example a short between the two leads 202, 203 may produce an error code in the generator 130 and the system may shut down safely.

In an alternate example, also depicted by FIG. 5, the relay 210 may be a normally closed relay that participates in the conduction path of one of the electrical leads 202 or 203. Prior to reaching the predetermined count the relay 210 would be closed; allowing current to flow through the therapy circuit 132'. Upon reaching the count value or satisfying another deactivation pattern, the relay 210 would open creating a break in the electrical leads 202, 203 in the circuit and preventing the circuit from carrying electricity. The therapy circuit 132' would become non-operational.

In implementing the count approach, the termination circuit 1162 circuit may have a storage capacitor 218 that stores a charge from the leads 200 and 201 (which may be the therapy circuit 132' or the control circuit 134') and delivers a voltage to the programmable integrated circuit chip 1163. A small value of the capacitor 218 may result in a stored charge that dissipates nearly instantaneously. In this case the chip 1163 may count for the period of time that the input AC signal is activated. The countdown circuit would effectively measure the amount of time that the therapy circuit 132 is energized, or the aggregate duration of the leads 200 and 201 being energized.

Alternately the storage capacitor 218 may be larger so as to feed the chip 1163 for a finite amount of time after the leads 200 and 201 are activated. In one example, the storage capacitor 218 may be sized to discharge a voltage to the integrated chip for a time longer than the predetermined count time in the chip 1163. In this case the termination circuit 1162 would effectively measure elapsed time from the first activation of the leads 200 and 201. Alternatively, the storage capacitor may be of an intermediate size to suit an expected manner of usage and define an appropriate deactivation pattern. Therefore, the storage capacitor defining the storage element is implemented such that either the storage capacitor can be large enough to effectively monitor elapsed time, or the storage capacitor sized for instantaneous power, for implementing an aggregate use time approach to the termination event.

Figure 6A:
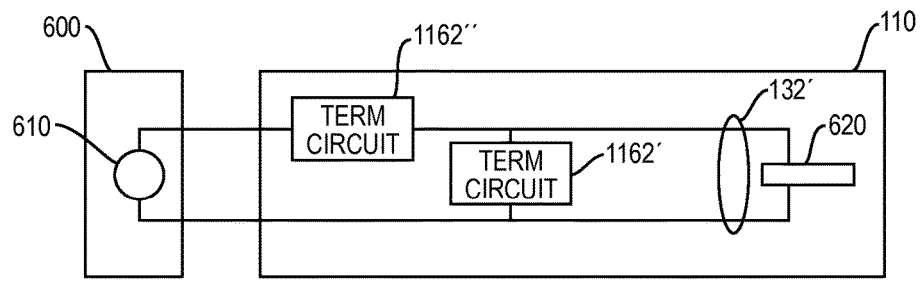
FIGS. 6a and 6b show configurations of the termination circuit in a powered surgical device and an electrode based approach, respectively.
Figure 6B:
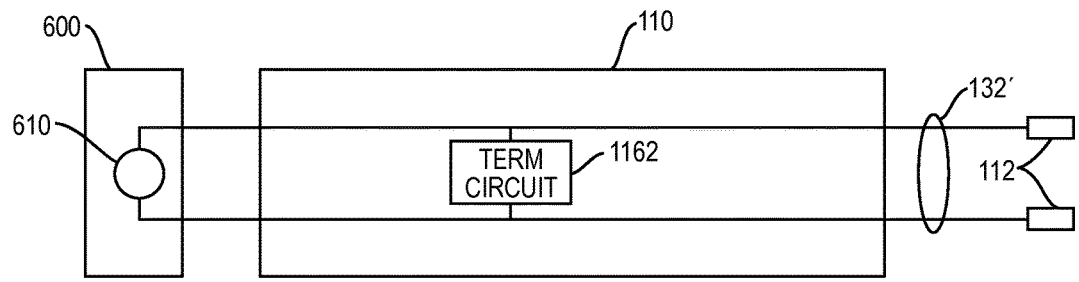

FIGS. 6a and 6b show configurations of the termination circuit in a powered surgical device and an electrode based approach, respectively. Referring to FIGS. 4-6b, the surgical device 110 includes the termination circuit 1162, which may be in parallel 1162' or series 1162" arrangement with a console power source 610 from a distal console 600, such as the generator 130. FIG. 6a depicts a powered surgical element (PSE) 620, such as an electric (AC or DC) motor or other suitable electrical appliance. FIG. 6b depicts a matched pair of bipolar electrosurgical electrodes 112 responsive to the power source 610. The power source 610 may define any suitable voltage or amperage for driving the PSE 620, electrodes 112 or other appliance, and may be suitable for also powering the termination circuit 1162, possible in conjunction with resistive elements for providing appropriate power. The termination circuit 1162 deenergizes or disables (by shorting or disconnecting) the therapy circuit 132'.

Figure 7:
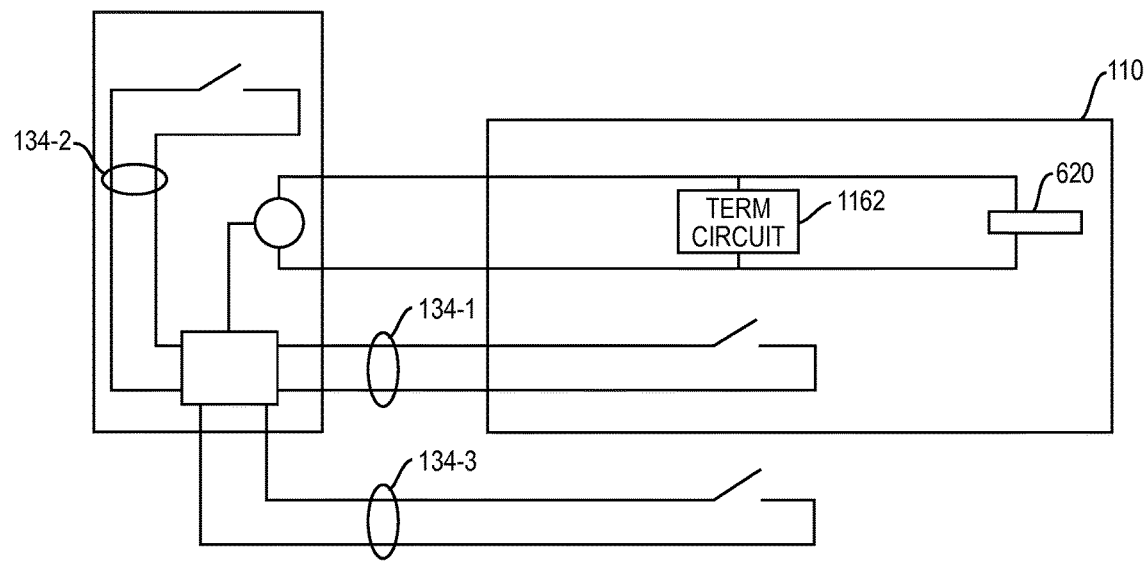
FIG. 7 shows a termination circuit in conjunction with various activation circuits.

FIG. 7 shows a termination circuit 1162 in conjunction with various control (activation) circuits 134'. As indicated above, the control circuit 134 directs the therapy circuit to 132 to energize for initiating operation of the PSE 620 (which may include electrodes 112). The control circuit 134 may take the form of a circuit 134'-1 on the hand-held device 110 (referring to control circuit 134' disposed in the enablement module 160 in the device 110 of FIGS. 3 and 4). Alternatively, a console mounted control circuit 134-2 or remote control circuit 134-3, such as a foot pedal or tethered button, may be employed.

In further detail, the medical device 110 may include, a powered surgical element 620, and a pair of leads 200, 201 adapted to connect the powered surgical element to a power source 610. The termination circuit 1162 is electrically coupled in a series or parallel manner to at least one lead of the pair of leads 200, 201. In an example configuration, the termination circuit 1162 includes a monitoring circuit 215, for identifying usage of the device 110 and determining when usage meets a predetermined deactivation pattern (criteria), and a deactivation circuit 222 for enforcing non-use. The monitoring circuit 215 is configured to detect a predetermined deactivation pattern by monitoring the current in the pair of leads 200, 201 until the predetermined activation pattern following a triggering event (such as initial power-up) is met. The deactivation circuit 222 is configured to interrupt one or more of the pair of leads 200, 201 for disabling the powered surgical element based on the occurrence of the predetermined deactivation pattern, such as by forcing the relay 210 into an open or closed mode to affect non-use. Therapy circuit leads 202, 203 may also be monitored for usage patterns. Since the medical device 110 is detachable from the console 600 containing the power source 610, monitoring and detection of the predetermined deactivation pattern cannot be usurped by reconnection to an alternate power source—the termination circuit 1162 is maintained in the device 110 as a stand-alone feature.

In the example of FIGS. 6a, 6b and 7, the powered surgical element 620 may be defined by any of a DC motor, an AC motor, a matched pair of bipolar electrosurgical electrodes or a monopolar electrode and complementary ground plate. The triggering event denoting first use and commencing the monitoring for the deactivation pattern includes at least one of a first time the powered surgical element is powered and an end of a duration of an initial time that the powered surgical element is first powered. Other options may be enforced, for example the predetermined deactivation pattern following the triggering event may include at least one of a duration of elapsed time, an aggregate duration of the time that current is applied to the powered surgical element, or a count of a discrete number of times current is applied to the powered surgical element, or a combination thereof.

Upon detection, the termination circuit 1162 interrupts one or more of the pair of leads by at least one of a short circuit between the pair of leads connected to the powered surgical element, or an open circuit in at least one of the pair of leads 200 . . . 203 depending on whether the control circuit 134', therapy circuit 132', or integration of both is monitored. In a console specific implementation, the powered surgical element 620 is configured to create an electrical signal that can be monitored by the console 600, and the deactivation circuit 222 interrupts one or more of the pair of leads 200-203 by adding or removing one or more electrical components to at least one of the pair of leads such that the electrical signal is altered for inducing an error state.

Figure 8:
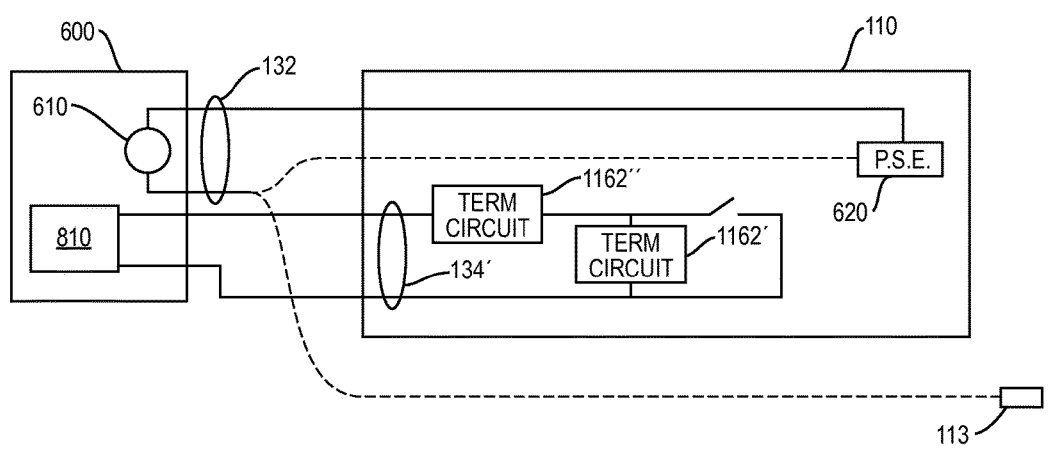
FIG. 8 shows a termination circuit with a co-located activation circuit and switch.

FIG. 8 shows a termination circuit with a co-located control (activation) circuit 134' and switch. Referring to FIGS. 5-8, the termination circuit 1162", 1162' connects in either series or parallel to the control circuit 134' in the device 110, and separate from the therapy circuit 132, which is driven by a controller 810 at the console 600 for powering the PSE 620, and optionally, the ground electrode 113 (FIG. 1). In the configuration of FIG. 8, the device 110 includes a powered surgical element 620, comprising: at least one powered surgical element lead 201 adapted for connecting the powered surgical element 620 to a power source 610, and an activation (control) circuit 134 configured to selectively provide an activation or enablement signal 144 to a controller 810 such that the controller 810 directs the power source 610 to provide power to the powered surgical element 610. The activation circuit 134 includes an activation switch 136' (FIG. 3) and a pair of activation circuit leads that connect the activation circuit 134 to the controller 810. A termination circuit 1162' or 1162" is electrically connected to at least one of the pair of activation circuit leads, in which the termination circuit 1162 further includes a monitoring circuit 215, and a deactivation circuit 222.

In short, the implementation of the controller 810 may be implemented as a comment logic circuit or distributed among several circuit or hardware elements. For example, there may be separate controllers—one that turns on the surgical power and the second that reads the activation switch signal. In general, the controller 810 may implement control or switching logic responsive to user controls or logic 163 for switching on the therapy circuit in response to user control until the termination circuit determines that the usage period has passed and usage should be prohibited/prevented as discussed above.

In the example of FIG. 8, the monitoring circuit 215 is configured to detect a triggering event and monitor the current in one or more of the pair of activation circuit leads connecting the activation circuit 134 until a predetermined deactivation pattern following the triggering event is met, such that the deactivation circuit 222 is operable to interrupt one or more of the pair of activation circuits leads for disabling the activation circuit based on the predetermined deactivation pattern. The deactivation pattern is therefore derived from the operation of the activation or control circuit 134, and independent of the application of the therapy circuit 132, which may be of a substantially higher voltage or current for providing therapeutic effects. The handheld medical device 110 including the PSE 620 remains detachable from the console 600 containing the power source so that the termination circuit 1162 continues to apply independently of disconnection from the console 600. Therefore, the activation circuit and termination circuits are adapted for connection to a plurality of independent power sources such as the power source 610 provided by the console 600.

Figure 9:
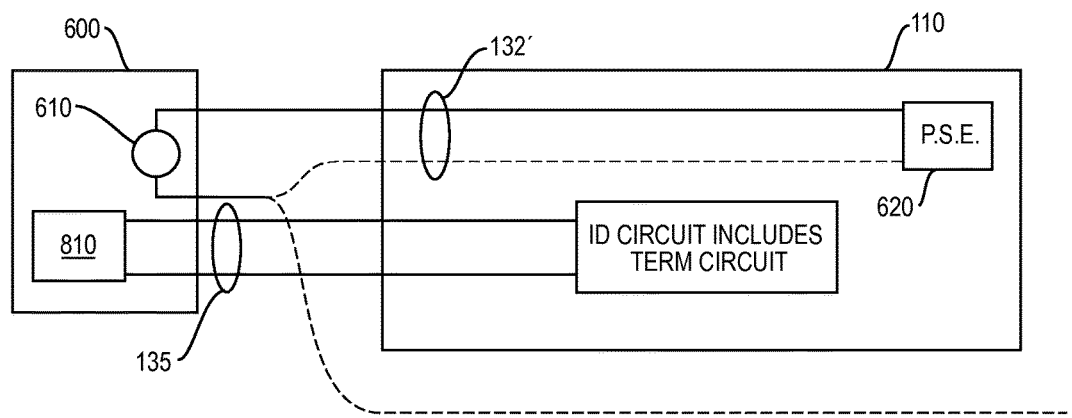
FIG. 9 shows an identification (ID) circuit in conjunction with a termination circuit.

FIG. 9 shows an identification (ID) circuit in conjunction with a termination circuit. Referring to FIGS. 3, 5 and 9, the medical device 110 includes the powered surgical element 620 and at least one powered surgical element lead that connect the power surgical element 620 to the power source 610. The device 110 also includes an identification circuit 135 configured to provide a signal 145 to the controller 810 such that the controller 810, upon recognizing the identification signal and an activation signal, provides instructions for the power source 610 to provide power to the powered surgical element 620. The identification circuit includes the monitoring circuit 215 and the deactivation circuit 222, such that monitoring circuit 215 detects a triggering event and monitors the identification circuit 145 until a predetermined deactivation pattern following the triggering event is met, and in response, the deactivation circuit 222 alters the identification circuit such that the identification signal 145 is altered to cause the controller to not provide instructions for the power source 610 to provide power to the powered surgical element 620. In other words, if the handheld device 110 is modified to avoid operation consistent with the deactivation pattern, or is switched with another console for reuse, the deactivation circuit 222 will nonetheless operate to prevent operation.

In various configurations, the triggering event may be the start of the initial time the identification circuit 135 is powered, rather than observing the therapy or control circuits. Also, the predetermined deactivation pattern following the triggering event may be a duration of elapsed time.

In another configuration the deactivation circuit 222 alters the identification circuit by one of creating a short circuit between the pair of id circuit leads, creating an open circuit in at least one of the pair of id circuit leads, and by adding or removing one or more electrical components to at least one of the pair of leads such that the electrical signal is altered so as to be read as an error state by the console.

In an operational scenario, the ID circuit calls for a proprietary controller to read it, to avoid usage with a handheld device 110 from a different vendor. Accordingly, the handheld device 110 may be a detachable medical device including powered surgical element 620 and an id circuit with an accompanying termination circuit 1162, having leads that connect the id circuit to the console and the PSE to a power source (which may or may not be in the console). Such a device is selectively attachable to the console 600, in which the console contains the a controller 810 for reading an ID signal from an ID circuit in detachable/replaceable medical device and an activation signal from an activation circuit that may be in the device, in the console, or wired externally to the console. Upon reading these signals the controller 810 instructs a power source (that may also be in the console) to supply power to a powered surgical element in the device.

Figure 10:
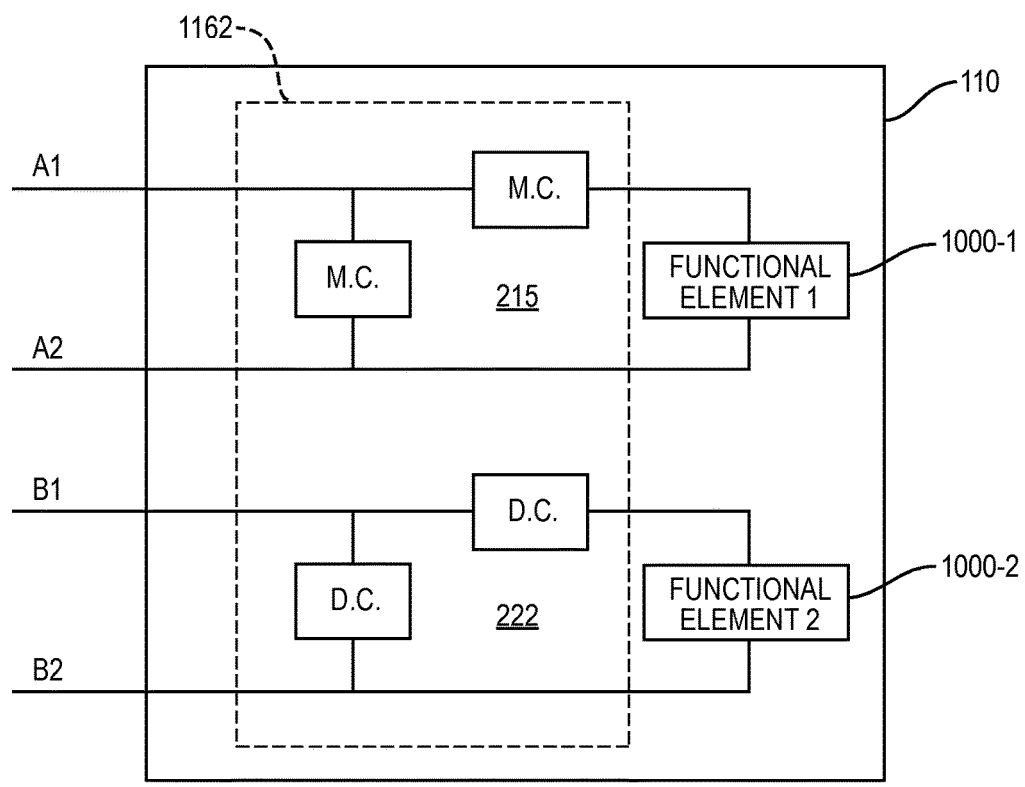
FIG. 10 shows alternate configurations of the therapy circuit, activation circuit and termination circuit.

FIG. 10 shows an alternate configuration of the therapy circuit, activation circuit, ID circuit and termination circuit. The configuration of FIG. 10 modularizes the monitoring circuit 215 and deactivation circuit 222 to operate with any of the therapy circuit (powered surgical element circuit) 132', control circuit (activation circuit) 134', and ID circuit 135'. Referring to FIGS. 3, 5 and 9-10, the handheld medical device 110 includes one or more functional elements 1000-1 . . . 1000-2 (1000 generally), of which one is a PSE 620 and the other is at least one of the control circuit 134', or ID circuit 135', where the monitoring circuit 215 and the deactivation circuit 222 each connect to one of the functional elements 1000. In other words, the device 110 includes at least one powered surgical element lead that connect the power surgical element to a power source, and at least one of a control (activation) circuit 132' comprising a pair of activation circuit leads that connect the activation circuit to a controller 810, and an identification circuit 135 comprising a pair of identification circuit leads that connect the activation circuit to the controller 810.

The termination circuit 1162 includes the monitoring circuit 215 electrically connected to one of the at least one powered surgical element lead, one of the pair of activation circuit leads, and one of pair of identification circuit leads, and the deactivation circuit 222 electrically connected to a different one of the at least one powered surgical element lead, one of the pair of activation circuit leads, and one of pair of identification circuit leads. Operation is then such that the monitoring circuit 215 detects a triggering event and monitors a portion of the current in the device 110 until a predetermined deactivation pattern following the triggering event is met, and the deactivation circuit 222 renders the device incapable of providing power to the powered surgical element, contained in the handheld medical device 110 configured to detach from a console 600 containing the controller 810.

Configurations disclosed herein include at least some features that may be implemented by a computer or similar processor based set of programmed instructions. Alternate configurations of the invention may therefore include a multiprogramming or multiprocessing computerized device such as a multiprocessor, controller or dedicated computing device in either a handheld, mobile, or desktop form or the like configured with software and/or circuitry (e.g., a processor as summarized above) to process any or all of the method operations disclosed herein as embodiments of the invention. Still other embodiments of the invention include software programs such as a Java Virtual Machine and/or an operating system that can operate alone or in conjunction with each other with a multiprocessing computerized device to perform the method embodiment steps and operations summarized above and disclosed in detail below. One such embodiment comprises a computer program product that has a non-transitory computer-readable storage medium including computer program logic encoded as instructions thereon that, when performed in a multiprocessing computerized device having a coupling of a memory and a processor, programs the processor to perform the operations disclosed herein as embodiments of the invention to carry out data access requests. Such arrangements of the invention are typically provided as software, code and/or other data (e.g., data structures) arranged or encoded on a computer readable medium such as an optical medium (e.g., CD-ROM), floppy or hard disk or other medium such as firmware or microcode in one or more ROM, RAM or PROM chips, field programmable gate arrays (FPGAs) or as an Application Specific Integrated Circuit (ASIC). The software or firmware or other such configurations can be installed onto the computerized device (e.g., during operating system execution or during environment installation) to cause the computerized device to perform the techniques explained herein as embodiments of the invention.

While the system and methods defined herein have been particularly shown and described with references to embodiments thereof, it will be understood by those skilled in the art that various changes in form and details may be made therein without departing from the scope of the invention encompassed by the appended claims.

What is claimed is:

1. A medical device, comprising;
a powered surgical element;
at least one powered surgical element connection adapted for connecting the powered surgical element to a power source;
an activation circuit configured to selectively provide an activation signal to a controller such that the controller directs the power source to provide power to the powered surgical element, the activation circuit including:
an activation switch;
a pair of activation circuit connections that connect the activation circuit to the controller; and
a termination circuit electrically connected to at least one of the pair of activation circuit connections, the termination circuit further comprising:
a monitoring circuit; and
a deactivation circuit,
the monitoring circuit configured to detect a triggering event and monitor the current in one or more of the pair of activation circuit connections until a predetermined deactivation pattern following the triggering event is met, the deactivation circuit operable to interrupt one or more of the pair of activation circuits connections for disabling the activation circuit based on the predetermined deactivation pattern, the triggering event defined by a first time the powered surgical element is powered on and the deactivation pattern is based on count of a discrete number of times current is applied to the powered surgical element or an aggregate duration of the time that current is applied to the powered surgical element;
the medical device being detachable from a console containing the power source.

2. The medical device of claim 1 wherein the console contains the controller.

3. The powered surgical element of claim 1 wherein the activation circuit and termination circuit are each adapted for connection to independent power sources.

4. The device of claim 1 wherein the termination circuit is configured to interrupt a current flowing to the powered surgical element by disabling the activation circuit.

5. The device of claim 1 wherein the termination circuit is configured to interrupt a current flowing to the powered surgical element by disabling the therapy circuit or activation circuit.

6. The medical device of claim 1 wherein:
the deactivation pattern is based on count of a discrete number of times current is applied to the powered surgical element.

7. The medical device of claim 1 wherein:
the deactivation pattern is based on an aggregate duration of the time that current is applied to the powered surgical element.

8. The medical device of claim 1 wherein:
the predetermined deactivation pattern is based on a duration of elapsed time that current is applied to the powered surgical element.

9. A medical device, comprising:
an identification circuit configured to provide an identification signal to a controller such that the controller, upon recognizing the identification signal and an activation signal, provides instructions for a power source to provide power to a powered surgical element;
the identification circuit comprising:
a monitoring circuit; and
a deactivation circuit,
the monitoring circuit configured to detect a triggering event and monitor the identification circuit until a predetermined deactivation pattern following the triggering event is met, and the deactivation circuit alters the identification circuit such that the identification signal is altered to cause the controller to not provide instructions for the power source to provide power to the powered surgical element,
the triggering event being defined by a first time the powered surgical element is powered on and the deactivation pattern is based on one of:
a count of a discrete number of times current is applied to the powered surgical element,
an aggregate duration of the time that current is applied to the powered surgical element, and
a duration of elapsed time; and
the medical device configured to detach from a console containing the controller, wherein:
the deactivation circuit is configured to alter the identification circuit by creating an open circuit in at least one of the pair of identification circuit connections so as to be read as an error state by the console.

10. The medical device of claim 9 wherein the triggering event is the start of the initial time that the identification circuit is powered.

11. A medical device, comprising:
an identification circuit configured to provide an identification signal to a controller such that the controller, upon recognizing the identification signal and an activation signal, provides instructions for a power source to provide power to a powered surgical element;
the identification circuit comprising:
a monitoring circuit; and
a deactivation circuit,
the monitoring circuit configured to detect a triggering event and monitor the identification circuit until a predetermined deactivation pattern following the triggering event is met, and the deactivation circuit alters the identification circuit such that the identification signal is altered to cause the controller to not provide instructions for the power source to provide power to the powered surgical element,
the triggering event being defined by a first time the powered surgical element is powered on and the deactivation pattern is based on one of:
a count of a discrete number of times current is applied to the powered surgical element,
an aggregate duration of the time that current is applied to the powered surgical element, and
a duration of elapsed time; and
the medical device configured to detach from a console containing the controller, wherein the predetermined deactivation pattern following the triggering event is a duration of elapsed time, the deactivation circuit configured to alter the identification circuit by one of creating a short circuit in the identification circuit, creating an open circuit in at least one of the pair of identification circuit connections, and by adding or removing one or more electrical components to at least one of the pair of identification circuit connections such that the electrical signal is altered so as to be read as an error state by the console.

12. A medical device, comprising:
an identification circuit configured to provide an identification signal to a controller such that the controller, upon recognizing the identification signal and an activation signal, provides instructions for a power source to provide power to a powered surgical element;

the identification circuit comprising:
- a monitoring circuit; and
- a deactivation circuit, the monitoring circuit configured to detect a triggering event and monitor the identification circuit until a predetermined deactivation pattern following the triggering event is met, and the deactivation circuit alters the identification circuit such that the identification signal is altered to cause the controller to not provide instructions for the power source to provide power to the powered surgical element, the triggering event being defined by a first time the powered surgical element is powered on and the deactivation pattern is based on one of:
- a count of a discrete number of times current is applied to the powered surgical element,
- an aggregate duration of the time that current is applied to the powered surgical element, and
- a duration of elapsed time; and the medical device configured to detach from a console containing the controller, wherein:

the deactivation circuit is configured to alter the identification circuit by by adding or removing one or more passive electrical components to at least one of the pair of identification circuit connections such that the electrical signal is altered so as to be read as an error state by the console.

* * * * *